United States Patent
Kamiyama

(10) Patent No.: US 8,499,636 B2
(45) Date of Patent: *Aug. 6, 2013

(54) ULTRASONIC DIAGNOSTIC APPARATUS AND IMAGE PROCESSING APPARATUS

(75) Inventor: Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 201 days.

This patent is subject to a terminal disclaimer.

(21) Appl. No.: 12/884,984

(22) Filed: Sep. 17, 2010

(65) Prior Publication Data

US 2011/0004097 A1    Jan. 6, 2011

Related U.S. Application Data

(60) Division of application No. 11/924,199, filed on Oct. 25, 2007, now Pat. No. 7,886,603, which is a continuation of application No. 10/832,356, filed on Apr. 27, 2004, now Pat. No. 7,302,850.

(30) Foreign Application Priority Data

Apr. 28, 2003 (JP) ................................. 2003-124168

(51) Int. Cl.
G01N 29/07 (2006.01)
(52) U.S. Cl.
USPC .............................................. 73/606; 73/629
(58) Field of Classification Search
USPC ............ 73/606, 607, 620, 629; 600/442–443, 600/447, 458
See application file for complete search history.

(56) References Cited

U.S. PATENT DOCUMENTS

| 5,215,094 A | 6/1993 | Franklin et al. |
| 5,873,830 A | 2/1999 | Hossack et al. |
| 5,951,478 A | 9/1999 | Hwang et al. |
| 5,971,928 A | 10/1999 | Dodd et al. |
| 6,080,107 A | 6/2000 | Poland |

(Continued)

FOREIGN PATENT DOCUMENTS

| JP | 8-140974 | 6/1996 |
| JP | 8-182680 | 7/1996 |

(Continued)

OTHER PUBLICATIONS

Jeff Powers, et al. "Microvascular Imaging of the Breast", The Eighth European Symposium on Ultrasound Contrast Imaging, Jan. 2003, p. 8.

(Continued)

Primary Examiner — J M Saint Surin
(74) Attorney, Agent, or Firm — Oblon, Spivak, McClelland, Maier & Neustadt, L.L.P.

(57) ABSTRACT

An ultrasonic diagnostic apparatus that performs high acoustic pressure and low acoustic pressure ultrasonic transmissions by switching at predetermined timing in the enhanced ultrasonography, and displays concurrently a replenishment image obtained through the low acoustic pressure transmission in real time like a moving picture, and a pre-flash image obtained through the low acoustic pressure transmission immediately before switching to the high acoustic pressure transmission like a still image to allow the operator to understand the structure at the level of capillaries. It is also possible to display a selected image obtained through the low acoustic pressure transmission at an arbitrary timing instead of the pre-flash image.

14 Claims, 13 Drawing Sheets

U.S. PATENT DOCUMENTS

| | | |
|---|---|---|
| 6,413,218 B1 | 7/2002 | Allison et al. |
| 6,582,370 B2 | 6/2003 | Jibiki |
| 6,641,538 B2 | 11/2003 | Nakaya et al. |
| 6,752,762 B1 | 6/2004 | DeJong et al. |
| 6,991,606 B2 | 1/2006 | Kamiyama |
| 7,006,955 B2 | 2/2006 | Daft et al. |
| 7,302,850 B2 | 12/2007 | Kamiyama |
| 7,588,547 B2 | 9/2009 | Deem et al. |
| 7,601,128 B2 | 10/2009 | Deem et al. |
| 7,886,603 B2 * | 2/2011 | Kamiyama ............. 73/606 |
| 2001/0056236 A1 | 12/2001 | Angelsen |
| 2002/0055681 A1 | 5/2002 | Averkiou et al. |
| 2004/0010194 A1 | 1/2004 | Kamiyama |
| 2009/0187107 A1 | 7/2009 | Yoshida |

FOREIGN PATENT DOCUMENTS

| | | |
|---|---|---|
| JP | 9-164138 | 6/1997 |
| JP | 11-89839 | 4/1999 |
| JP | 11-99152 | 4/1999 |
| JP | 11-137550 | 5/1999 |
| JP | 11-137552 | 5/1999 |
| JP | 11-155858 | 6/1999 |
| JP | 11-253449 | 9/1999 |
| JP | 2001-46373 | 2/2001 |
| JP | 2001-269341 | 10/2001 |
| JP | 2002-238901 | 8/2002 |
| JP | 2002-301078 | 10/2002 |
| JP | 2009-202017 | 9/2009 |
| WO | WO 02/102251 | 12/2002 |
| WO | WO 03/104843 | 12/2003 |
| WO | WO 03/105691 | 12/2003 |

OTHER PUBLICATIONS

Japanese Office Action issued Jul. 26, 2011, in Patent Application No. 2009-170436 (with English-language translation).

Office Action issued on Nov. 1, 2011 in the corresponding Japanese Patent Application No. 2009-170436 (with English Translation).

* cited by examiner

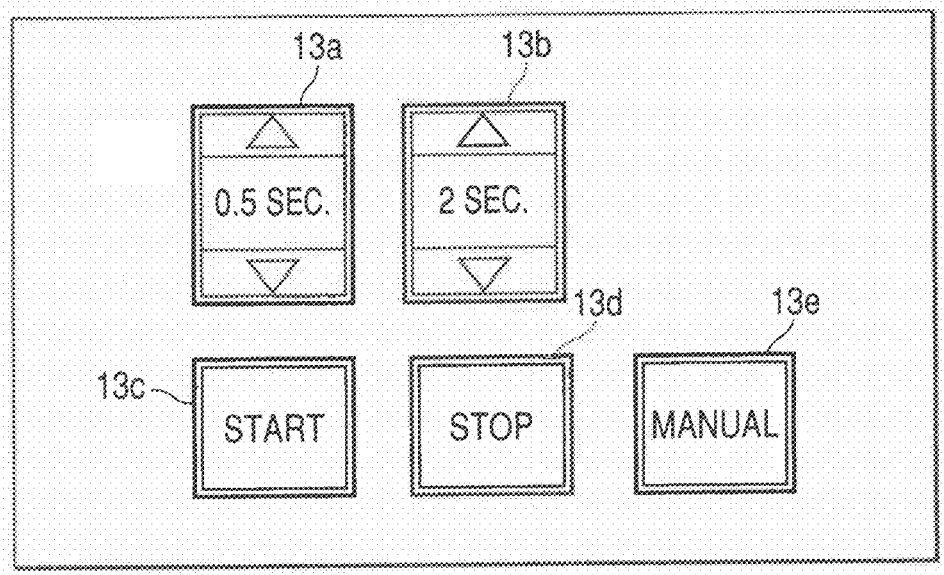

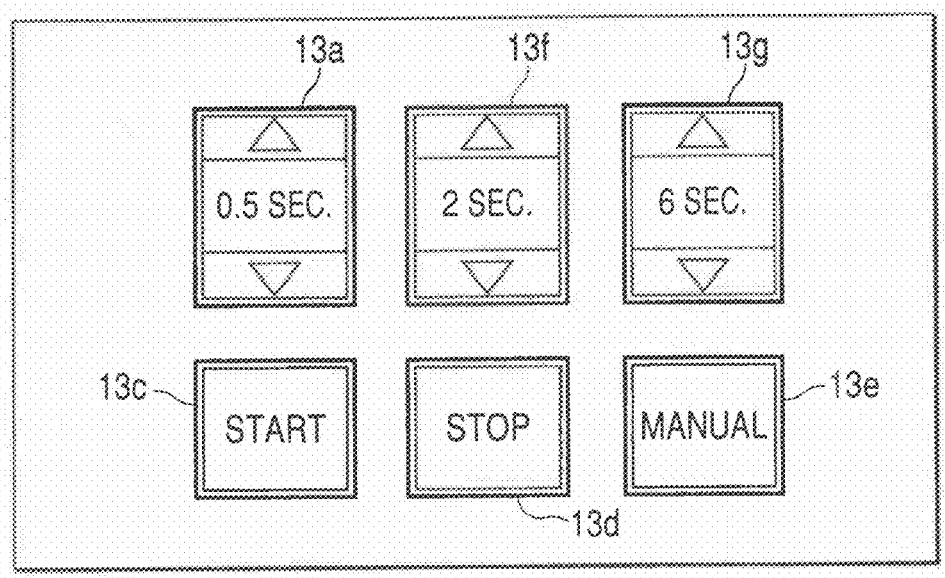

| n | Vc/V0 | DECIBELS |
|---|-------|----------|
| 1 | 0.632 | -1.99 |
| 2 | 0.393 | -4.05 |
| 3 | 0.283 | -5.47 |
| 4 | 0.221 | -6.55 |
| 5 | 0.181 | -7.42 |
| 6 | 0.154 | -8.14 |
| 7 | 0.133 | -8.76 |
| 8 | 0.118 | -9.30 |

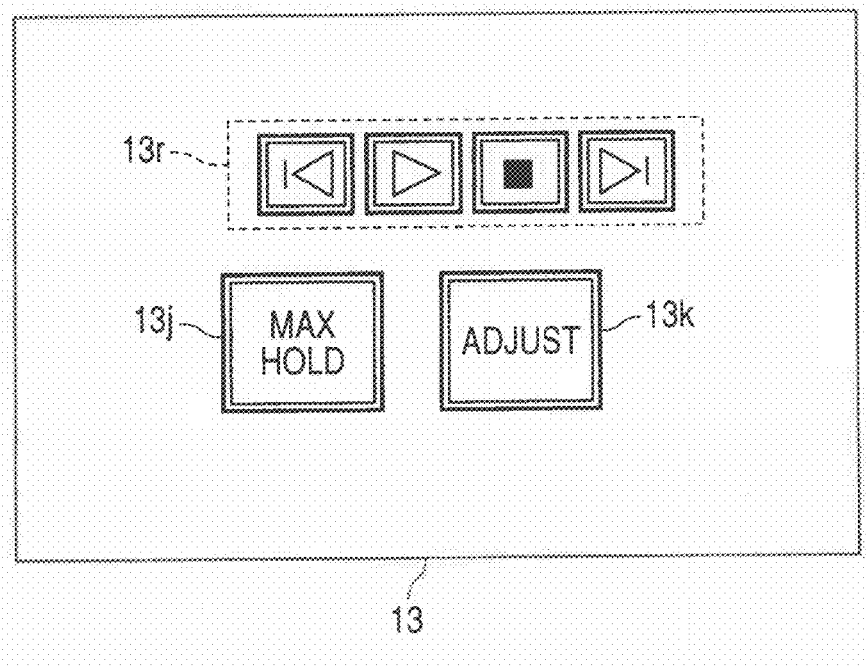

ULTRASONIC DIAGNOSTIC APPARATUS AND IMAGE PROCESSING APPARATUS

CROSS-REFERENCE TO RELATED APPLICATIONS

This application is a divisional of U.S. application Ser. No. 11/924,199 filed Oct. 25, 2007, which is a continuation of U.S. application Ser. No. 10/832,356 filed Apr. 27, 2004, and is based upon and claims the benefit of priority from prior Japanese Patent Application No. 2003-124168, filed Apr. 28, 2003, the entire contents of each of which are incorporated herein by reference.

BACKGROUND OF THE INVENTION

1. Field of the Invention

The present invention is in the field of the enhanced ultrasonography using an ultrasound contrast medium, and relates to an ultrasonic diagnostic apparatus and an image processing apparatus capable of presenting, as diagnostic information, a microcirculation at the level of capillaries and the microstructure of a vascular flow relatively fast compared with capillaries.

2. Description of the Related Art

An ultrasonic diagnosis is convenient in that beat pulsations of the heart or motions of a fetus can be obtained as a real-time display through a manipulation as simple as placing an ultrasonic probe to the body surface, and a screening can be performed repetitively due to its high safety; moreover, owing to its small system size in comparison with other diagnosis apparatus for X-ray imaging, CT imaging, MRI, etc., the ultrasonic diagnosis apparatus can be moved to a bedside, so that a screening can be readily performed at the bedside. Although the ultrasonic diagnostic apparatus varies with kinds of functions furnished therewith, the one small enough for an individual to carry around with one hand has been developed, and different from X-ray imaging or the like, an ultrasonic diagnosis has no exposure risk. The foregoing advantages enable the use of an ultrasonic diagnosis in the obstetrics department, home medical care, etc.

An intravenous ultrasound contrast medium has been commercialized, and the enhanced ultrasonography is thus being performed in recent years. This method aims to evaluate the dynamic state of a blood flow when examining, for example, the heart or liver by enhancing blood flow signals with the aid of an ultrasound contrast medium injected intravenously. In most of the contrast media, micro bubbles function as the reflection source. Bubbles, being a delicate material by nature, rupture upon ultrasonic irradiation, even at the ordinary diagnostic level, due to the mechanical function, which results in a decrease in signal strength from the scan surface. In order to observe the circulation dynamically in real time, it is therefore necessary to reduce the scan-caused disruption of bubbles relatively, for example, by producing an image through an ultrasonic transmission at a low acoustic pressure. Imaging through such a low acoustic pressure ultrasonic transmission reduces a signal-to-noise ratio (S/N ratio) as well, and various signal processing methods have been proposed to compensate for such a reduction.

Also, by exploiting the characteristic that the contrast medium bubbles rupture as described above, a method as follows has been proposed. That is, the method includes (A) observing the dynamic state of bubbles filling the scan plane under low acoustic pressure irradiation; (B) destroying bubbles within the plane (to be more exact, within the volume being irradiated) by switching the irradiation acoustic pressure to a high acoustic pressure, and (C) observing a way in which bubbles flow into the plane again. This method is disclosed, for example, in JP-A-11-155858, and is generally referred to as the replenishment method.

Incidentally, a representative diagnostic image extracted by the enhanced ultrasonography is roughly divided to two types. One is a diagnostic image of a relatively fast, thick blood vessel, and the other is a diagnostic image for a tiny blood flow at the level of capillaries (in the case of the liver, a blood flow giving rise to perfusion in the sinusoidal space). Problems with these images are that it is difficult to extract micro-vascular branches on the former vascular image, whereas in the latter, although signals from micro vessels are detected, the vascular branches are not extracted due to the limit of spatial resolution and merely an increase in luminance can be confirmed as a domain. In short, both the images fail to extract micro-vascular branches at the intermediate level. Blood flow information at this level, however, indicates the degree of progress of the shunt of vessels, regenerative nodules, etc., and is therefore said to be information of great importance for a differential diagnosis of a diffuse liver disease or a liver cancer.

BRIEF SUMMARY OF THE INVENTION

The invention was devised in view of the foregoing problems, and therefore has an object to provide an ultrasonic diagnostic apparatus and an image processing apparatus capable of extracting diagnostic information at the level of micro-vascular branches rapidly in an effective manner.

The present invention may provide an ultrasonic diagnostic apparatus that obtains an ultrasonic image by scanning, by means of ultrasonic waves, a specific region of a subject injected with contrast medium bubbles, which includes: an ultrasonic probe to transmit an ultrasonic wave to the subject and receive an echo signal from the ultrasonic wave; a transmission unit to perform, via the ultrasonic probe, a first ultrasonic transmission for one frame plural times at a first acoustic pressure, which is an acoustic pressure not to destroy the contrast medium bubbles but to obtain an image of a blood flow circulation, and to perform a second ultrasonic transmission at a second acoustic pressure to destroy the contrast medium bubbles; a control unit to control the transmission unit in such a manner that the plural first ultrasonic transmissions and the second ultrasonic transmission are performed alternately; an image generating unit to generate a first display image by performing a luminance value holding computation using echo signals of at least two frames obtained through the plural first ultrasonic transmissions; and a display unit to display the first display image.

The present invention may provide an ultrasonic diagnostic apparatus that obtains an ultrasonic image by scanning, by means of ultrasonic waves, a specific region of a subject injected with contrast medium bubbles, which includes: an ultrasonic probe to transmit an ultrasonic wave to the subject and receive an echo signal from the ultrasonic wave; a transmission unit to perform, via the ultrasonic probe, a first ultrasonic transmission for one frame plural times at a first acoustic pressure, which is an acoustic pressure not to destroy the contrast medium bubbles but to obtain an image of a blood flow circulation, and to perform a second ultrasonic transmission at a second acoustic pressure to destroy the contrast medium bubbles; a control unit to control the transmission unit in such a manner that the plural first ultrasonic transmissions and the second ultrasonic transmission are performed alternately; an image generating unit to generate a first display image by performing a luminance value holding computation using echo signals of at least two frames obtained through the plural first ultrasonic transmissions; and a display unit to display the first display image by comparing an echo signal $P_0$ at each position of a reference frame, obtained through the first ultrasonic transmission immediately before switching to the second ultrasonic transmission, with an echo signal $P_i$ at each coordinate of respective frames obtained through the plural first ultrasonic transmissions, and changing a display mode including a hue, saturation, brightness, and so forth of the first display image for a coordinate corresponding to an echo signal $P_i$ satisfying a relation, $P_i/P_0 \geq (e^{1/n}-1)/e^{1/n}$ (n is a natural number).

The present invention may provide an image processing apparatus, including: a storage unit to store data related to ultrasonic images of at least two frames obtained through scanning by means of ultrasonic waves at a first acoustic pressure, which is an acoustic pressure not to destroy contrast medium bubbles but to obtain an image of a blood flow circulation, immediately after a first ultrasonic transmission at a first acoustic pressure to destroy the contrast medium bubbles; an image generating unit to generate a first display image by performing a luminance value holding computation, using data related to the ultrasonic images of at least two frames; and a display unit to display the first display image.

BRIEF DESCRIPTION OF THE SEVERAL VIEWS OF THE DRAWING

FIG. 8 is a view showing an example of switches, buttons, etc. provided to an input device 13;

FIG. 10 is a view showing another example of switches, buttons, etc. provided to the input device 13;

FIG. 18 is a view showing still another example of switches, buttons, etc. provided to the input device 13.

DETAILED DESCRIPTION OF THE INVENTION

Figure 1:
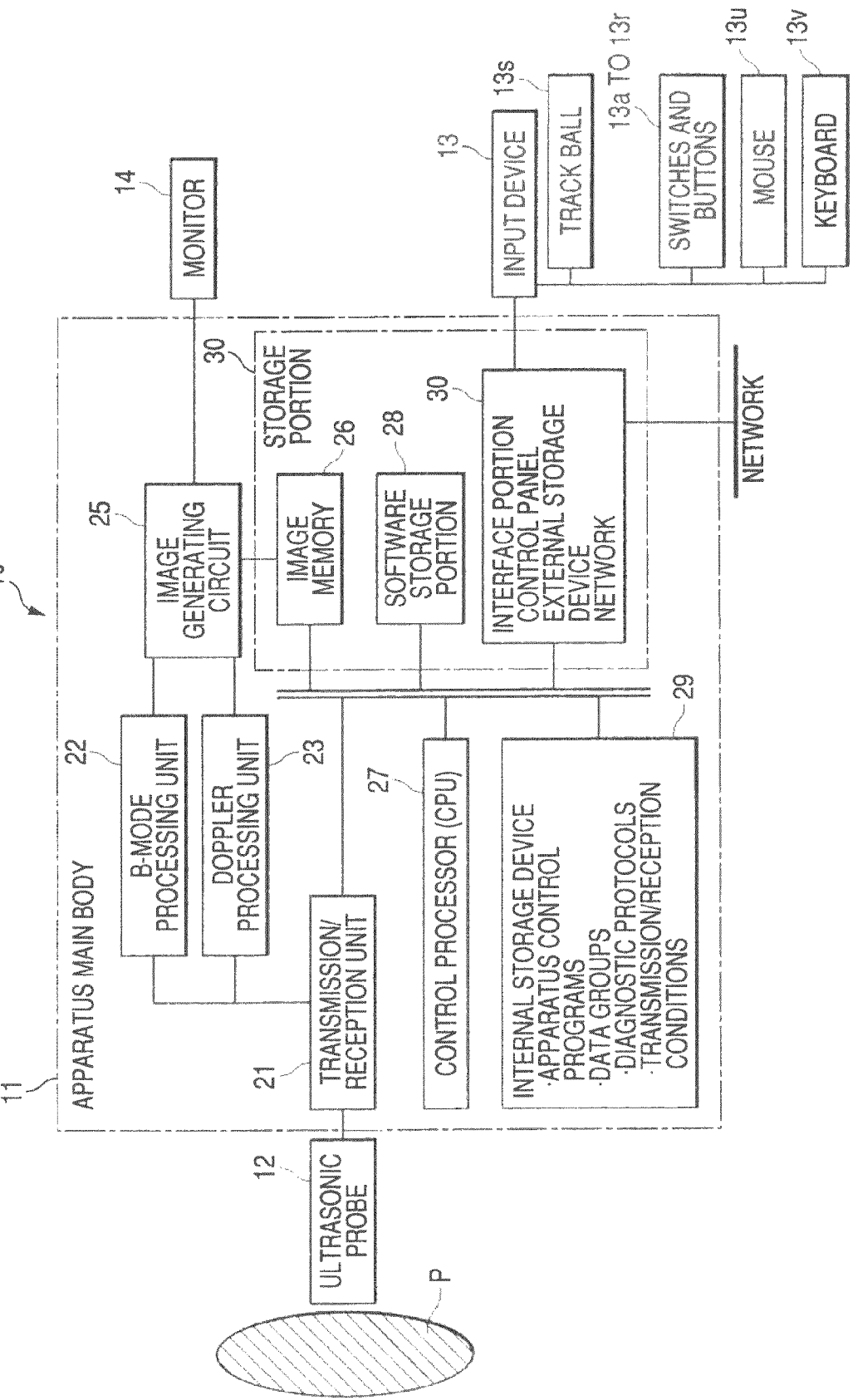
FIG. 1 is a block diagram showing the configuration of an ultrasonic diagnostic apparatus 10 according to the invention.

A first embodiment and a second embodiment of the invention will now be described with reference to the accompanying drawings. Hereinafter, components having substantially the same functions and configurations will be labeled with the same reference numerals, and the description of such components will not be repeated unless the necessity arises.

First Embodiment

FIG. 1 is a block diagram showing the configuration of an ultrasonic diagnostic apparatus 10 of this embodiment. As is shown in the drawing, the ultrasonic diagnostic apparatus 10 includes an ultrasonic probe 12, an input device 13, a monitor 14, a transmission/reception unit 21, a B-mode processing unit 22, a Doppler processing unit 23, an image generating circuit 25, an image memory 26, a control processor 27, a software storage portion 28, an internal storage device 29, and an interface portion 30. The ultrasonic transmission/reception unit 21 and the like built into the apparatus main body 11 may be in the form of hardware, such as integrated circuits, or they may be in the form of softwarily modularized software programs. The following description will describe functions of the components individually.

The ultrasonic probe 12 includes: plural piezoelectric transducers that generate ultrasonic waves according to a driving signal from the ultrasonic transmission/reception unit 21 and convert reflection waves from the subject to electrical signals; matching layers provided to the piezoelectric transducers; backing materials used to prevent backward propagation of ultrasonic waves from the piezoelectric transducers, etc. When an ultrasonic wave is transmitted to the subject P from the ultrasonic probe 12, the transmitted ultrasonic wave reflects consecutively on the discontinuous surfaces of acoustic impedance in tissues of the body, and reflections are received at the ultrasonic probe 12 as echo signals. The amplitude of the echo signals depends on a difference in acoustic impedance between the discontinuous surfaces on which reflection takes place. In a case where transmitted ultrasonic pulses are reflected on the surface of a blood flow, the heart wall or the like in motion, the echoes undergo frequency deviation by the Doppler effect, depending on the rate components of the moving substance in the ultrasonic transmission direction.

The input device 13 is connected to the apparatus main body 11, and includes various switches and buttons, a track ball 13s, a mouse 13c, a keyboard 13d, etc. through which the operator inputs all sorts of instructions, conditions, setting instructions of the region of interest (ROI), setting instructions of various image quality conditions, etc. into the apparatus main body 11.

The monitor 14 displays the morphologic information and blood flow information in the living body in the form of images according to video signals from the image generating circuit 25.

The transmission/reception unit 21 includes a trigger generating circuit, a delay circuit, a pulsar circuit, etc., all of which are not shown in the drawing. The pulsar circuit repetitively generates a rate pulse used to generate an ultrasonic wave to be transmitted, at a predetermined rate frequency, fr Hz (cycle: 1/fr sec.) The delay circuit gives each rate pulse a delay time needed to focus an ultrasonic wave to a beam shape and determine the transmission directivity for each channel. The trigger generating circuit impresses a driving pulse to the probe 12 at the timing based on the resulting rate pulse.

In order to perform a scan sequence described below at a command from the control processor 27, the transmission/reception unit 21 is furnished with a function of changing instantaneously a transmission frequency, a transmission driving voltage, etc. The transmission driving voltage, in particular, can be changed by a linear amplifier type oscillation circuit capable of switching its value instantaneously or a mechanism that electrically switches plural power supply units.

In addition, the transmission/reception unit 21 includes an amplifier circuit, an analog-to-digital converter, an adder, etc., all of which are not shown in the drawing. The amplifier circuit amplifies an echo signal captured via the probe 12 for each channel. The analog-to-digital converter gives the amplified echo signal a delay time needed to determine the reception directivity, after which the adder performs addition processing. The addition enhances the reflection components of the echo signals in a direction corresponding to the reception directivity, and the reception directivity and the transmission directivity together form an integrated beam for ultrasonic transmission and reception.

The B-mode processing unit 22 receives an echo signal from the transmission/reception unit 21, applies logarithmic amplification, envelope detection processing, etc. on the echo signal, and thereby generates data in which the signal strength is represented by the brightness of luminance. The data thus generated is sent to the image generating circuit 25, and displayed on the monitor 14 as a B-mode image that shows the strength of the reflection wave by luminance.

The Doppler processing unit 23 performs frequency analysis on the rate information from the echo signal received from the transmission/reception unit 21 to extract a blood flow, tissues, and contrast medium echo components due to the Doppler effect, and thereby finds blood flow information, such as the average rate, dispersion, and power, at a number of points. The blood flow information thus obtained is sent to the image generating circuit 25, and displayed in color on the monitor 14 as an average rate image, a dispersion image, or a power image, either solely or in combination.

The image generating circuit 25 converts a sequence of scanning line signals of ultrasound scans to a sequence of scanning line signals of a general video format typically used in TV sets or the like, and thereby generates an ultrasonic diagnostic image as a display image. The image generating circuit 25 has a built-in storage memory that stores image data, so that, for example, the operator is able to retrieve an image recorded during the screening after the diagnosis was made. Data before entering the image generating circuit 25 is also referred to as raw data.

Figure 2:
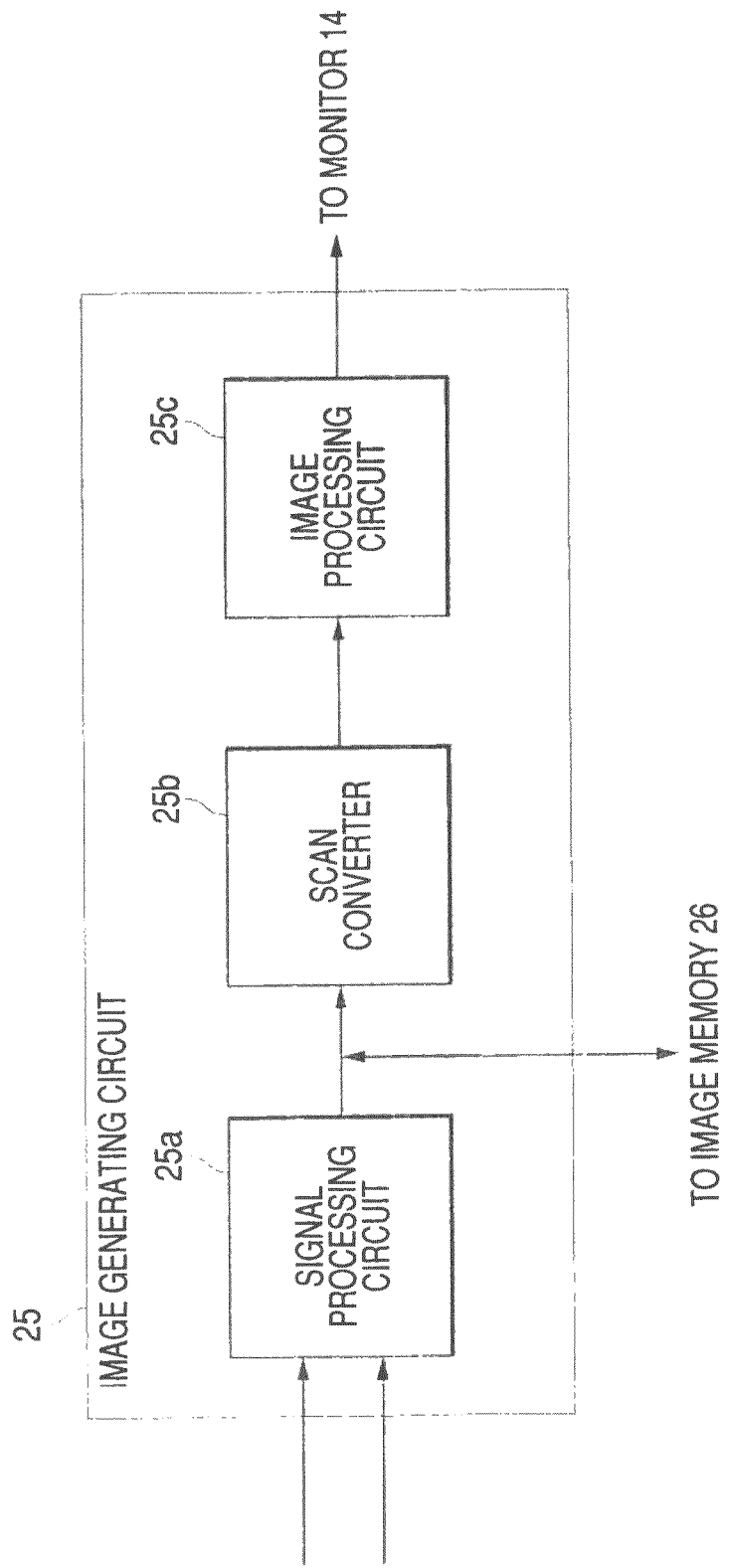
FIG. 2 is a view used to explain an image generating circuit 25 in detail.

FIG. 2 shows the image generating circuit 25 in detail. Initially, a signal processing circuit 25*a* performs filtering in such a manner that the image quality is determined at the level of a sequence of scanning line signals of ultrasound scans. An output from the signal processing circuit 25*a* is not only sent to a scan converter 25*b*, but also saved in the image memory 26. The scan converter 25*b* converts the sequence of scanning line signals of ultrasound scans into a sequence of scanning line signals of a general video format typically used in TV sets or the like. This output is sent to an image generating circuit 25*c*, which adjusts the luminance and contrast, performs image processing, such as spatial filtering, or synthesizes the output and character information and scales of various setting parameters, and outputs a resulting video signal to the monitor 14. A tomographic image showing the shape of tissues of the subject is thus displayed.

The image memory 26 comprises a storage memory used to store image data received from the signal processing circuit 25*a*. For example, the operator is able to retrieve the image data after the diagnosis was made, and the image data can be played back like a still image or the image data of plural frames can be played back like a moving picture. The image memory 26 also stores an output signal (referred to as a radio frequency (RF) signal) immediately after the ultrasonic transmission/reception unit 21, an image luminance signal having passed through the transmission/reception unit 21, other raw data, image data acquired via the network, etc. as necessity arises.

The internal storage device 29 saves a scan sequence described below, control programs to generate and display images, diagnostic information (patient ID, remarks of the physician, etc.), diagnostic protocols, transmission/reception conditions, a correspondence table shown in FIG. 15 (described below,) and other data groups. Also, the internal storage device 29 is used to save images in the image memory 26 when necessity arises. Data in the internal storage device 29 can be transferred to a peripheral apparatus via the interface circuit 30.

The control processor 27 functions as an information processing unit (computer), and also controls the operations of the main body of the ultrasonic diagnostic apparatus. The control processor 27 reads out a control program to generate and display an image or the like, which will be described below, from the internal storage device 29 to be developed on the software storage portion 28, and performs computations, control, etc. involved in various kinds of processing.

The interface portion 30 is an interface for the input device 13, the network, and a new external storage device (not shown). Data, analysis results, etc. of the ultrasonic images or the like obtained by the apparatus can be transferred to other devices by the interface portion 30 via the network.

(Scan Sequence)

A basic scan sequence that the ultrasonic diagnostic apparatus 10 performs will now be described with reference to FIG. 3A and FIG. 3B. The scan sequence of this embodiment (hereinafter, referred to simply as the scan sequence) is used in contrast echoes with the aid of a contrast medium to perform transmissions at two kinds of acoustic pressure alternately: a transmission at a high acoustic pressure (hereinafter, referred to as the high acoustic pressure (ultrasonic) transmission) to destroy contrast medium bubbles, and a transmission at a low acoustic pressure (hereinafter, referred to as the low acoustic pressure (ultrasonic) transmission) to obtain a diagnostic image by preventing the disruption of bubbles as much as possible. A suitable contrast medium used in imaging according to this sequence is a so-called next-generation contrast medium, bubbles of which keep releasing harmonic signals without being destroyed when ultrasonic waves are transmitted at a low acoustic pressure, thereby enabling imaging over a long time.

FIG. 3A is a view used to explain the scan sequence, in which the abscissa is used for time and the ordinate is used for a degree of mechanical function to the bubbles derived from transmissions. Also, each line represents an ultrasound scan related to one frame, and the length of each line represents the strength of mechanical function of a transmission acoustic pressure in each frame.

In other words, each line represents an ultrasound scan for one frame under the transmission conditions set in such a manner that as the length of each line in the longitudinal direction becomes longer (larger), the transmission frequency becomes lower or a transmission driving acoustic pressure becomes higher, or a combination thereof. Thus, longer lines 41 correspond to scans (three frames, in the case of the drawing) through high acoustic pressure irradiation, and shorter lines 43 correspond to scans through low acoustic pressure irradiation. Hereinafter, a tomographic image obtained through low acoustic pressure irradiation is referred to as a replenishment image. Also, of all the scans through low acoustic pressure irradiation, a tomographic image obtained from a frame scan 43a, a frame immediately before the switching to high acoustic pressure irradiation, is referred to as a pre-flash image.

Because one frame comprises plural scanning lines, one line symbolically represents a few hundreds transmissions and receptions related to plural scanning lines.

FIG. 3B is a view showing a change of the number of contrast medium bubbles with time when scans are performed according to the sequence of FIG. 3A. The abscissa (elapsed time) of FIG. 3B corresponds to the abscissa (elapsed time) of FIG. 3A. Generally, the number of contrast medium bubbles is thought to have a positive correlation with echo signals. Thus, as is shown in the drawing, because only a small number of contrast medium bubbles rupture under low acoustic pressure irradiation, the number of bubbles flowing into the scan plane increases gradually, and an equilibrium state is thereby achieved in the case of an observation over a long time. When the transmission is switched to the high acoustic pressure transmission, bubbles within the plane suddenly start to rupture, and the bubbles are eliminated almost completely through plural times of irradiation for one frame or more, preferably about 10 frames. By switching the transmission again to the low acoustic pressure transmission to observe a replenishment image, the operator becomes able to observe a way in which the replenishment takes place. By repetitively performing this procedure, it is possible to observe the replenishment phenomenon repetitively from the pre-flash image.

(Logical Background)

From the result of attempts in observing micro-vascular branches, the inventor discovered that a time duration during which information as to the contrast medium bubbles flowing into micro-vascular branches can be obtained is merely 1 to 2 sec. after the replenishment starts to takes place, and thereafter, dominating signals are those at the level of capillaries that cannot be resolved. On the other hand, however, micro-vascular branches cannot be extracted satisfactorily by merely displaying information within 1 to 2 sec. as a conventional ultrasonic diagnostic image. The reason why will be described with reference to FIG. 4 through FIG. 7. The hatchings in each figure symbolically indicate contrasted regions.

Figures 4, 5, 6, 7:
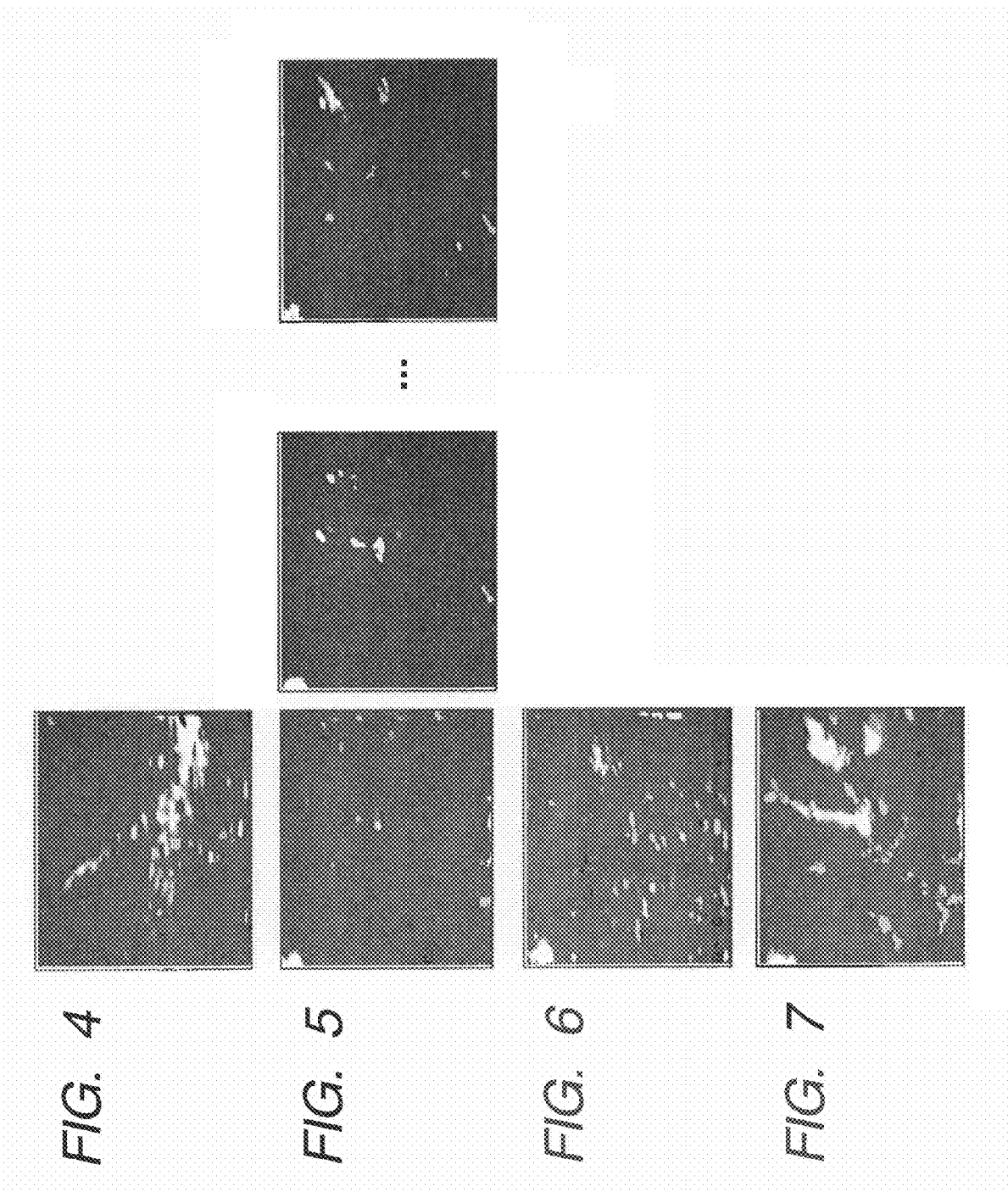
FIG. 4 shows an image of a (relatively thick) blood vessel into which a contrast medium flows abundantly.
FIG. 5 shows plural images of micro blood vessels through which a contrast medium flows less.
FIG. 6 shows a blood flow image on which even tiny blood flows are extracted.
FIG. 7 shows an image suitably presenting information of the structure (the vascular streams)

FIG. 4 shows an image of a vessel into which a contrast medium flows abundantly. A contrast medium flows abundantly into a relatively thick vessel, and such a vascular structure can be understood only from an image like the one shown in FIG. 4.

FIG. 5 shows plural images of micro vessels through which a contrast medium flows less. On an image like any of those shown in FIG. 5, bubbles are present sparsely in one image at a given moment, which makes it impossible to understand the vascular structure. Even when one observes time-sequential diagnostic images, he often fails to observe a continuous flow.

FIG. 6 shows a blood flow image on which even a tiny blood flow is extracted. On an image like the one shown in FIG. 6, as has been described, the vascular branches cannot be extracted due to the limit of spatial resolution, and only an increase in luminance is confirmed as a domain, which makes identification of micro-vascular branches impossible.

One advantage of this embodiment is that, as is shown in FIG. 7, an image suitably presenting information of a structure (the vascular streams, herein) can be provided as one kind of diagnostic information. To this end, a method of generating and displaying a diagnostic image and a diagnostic information extracting function, etc. as described below are performed.

(Generation and Display of Diagnostic Image)

The method of generating and displaying a diagnostic image (an image the apparatus actively displays as an image effective for diagnostic) achieved by the ultrasonic diagnostic apparatus 10 is roughly divided to two types. Firstly, a first image generating and displaying method for generating a replenishment image according to plural low acoustic pressure transmissions to be displayed in real time while displaying a pre-flash image concurrently with the replenishment image will be described.

In the pre-operation of imaging, a high acoustic pressure period ($T_H$ in FIG. 3) during which the high acoustic pressure ultrasonic transmission is performed, and a low acoustic pressure period ($T_L$ in FIG. 3) during which the low acoustic pressure ultrasonic transmission is performed are set to arbitrary values respectively by a switch 13a and a switch 13b of the input device 13 shown in FIG. 8. The drawing shows a case where the high acoustic pressure ultrasonic transmission is performed for 0.5 sec. followed by the low acoustic pressure ultrasonic transmission for 2.0 sec. Herein, seconds are used as a pre-set unit for $T_H$ and $T_L$; however, it may be configured in such a manner that these values are set in the unit of the number of frames.

By manipulating a start switch 13c after $T_H$ and $T_L$ are set, the scan sequence is started, according to which the high acoustic pressure ultrasonic transmission for $T_H$=0.5 sec. and the low acoustic pressure ultrasonic transmission for $T_L$=2 sec. Are performed repetitively. In this example case, a replenishment image obtained by these scans is displayed, and about 2 sec. later since the completion of the high acoustic pressure transmission, a pre-flash image is captured and displayed concurrently on the monitor 14.

Figure 9A:
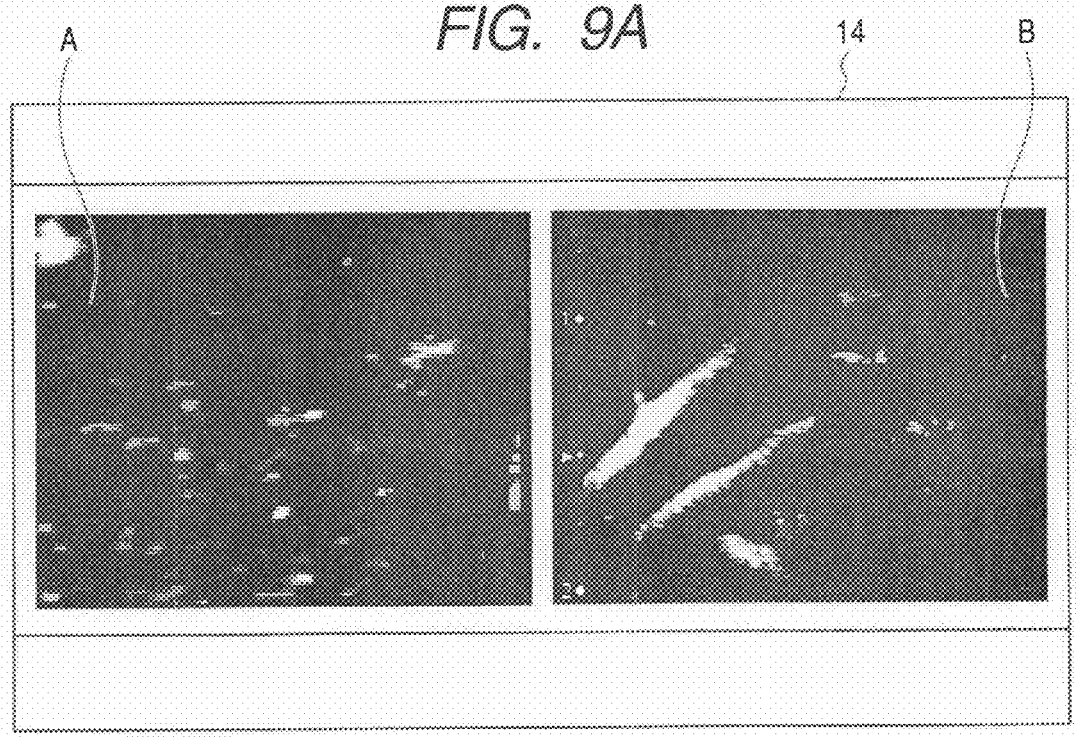
FIG. 9A is a view showing a monitor 14 on which a replenishment image A and a pre-flash image B are displayed concurrently.

FIG. 9A is a view showing the monitor 14 on which a pre-flash image A and a replenishment image B are displayed concurrently. On the monitor 14, the replenishment image B is displayed in real time like a moving picture, while the pre-flash image A is displayed like a still image. Also, when the transmission is switched to the following high acoustic pressure ultrasonic transmission or low acoustic pressure ultrasonic transmission, the replenishment image B or the pre-flash image A is sequentially updated to the latest image. The operator is thus able to observe in real time the replenishment state, in particular, a way in which the contrast medium flows into a fine perfusion at the level of capillaries, like a moving picture, while at the same time, he is able to observe the structure at the level of capillaries from the pre-flash image A being displayed like a still image.

The scans and the generation and display of images as described above are continued until the operator manipulates a stop switch 13d shown in FIG. 8. Alternatively, by manipulating a manual switch 13e, it is possible to perform the high acoustic pressure transmission alone for one shot (once) for a specified transmission time, without repetitively performing the high acoustic pressure transmission and the low acoustic pressure transmission.

A second image generating and displaying method will now be described. According to this method, a replenishment image related to the low acoustic pressure transmission at desired timing is generated as a diagnostic image to be displayed like a still image instead of the pre-flash image. Hereinafter, a replenishment image related to the low acoustic pressure transmission at desired timing and selected as a diagnostic image to be displayed like a still image is referred to as a selected image.

FIG. 10 is a view showing a switch group provided to the input device 13 used in the second image generating and displaying method. A selection time switch 13f allows the operator to arbitrary set timing (selection time $t_s$) at which the selected image is captured. In this example case, assume that the selection time $t_s$ is set to a time when a predetermined time has elapsed since the time (reference time) at which the last high acoustic pressure transmission is switched to the low acoustic pressure transmission and acquisition of a first image (reference image) during the low acoustic pressure period $T_L$ is started. Thus, in the case of FIG. 10, the selected image is captured 2 sec. later since the reference time.

Also, a switch 13g allows the operator to arbitrary set the low acoustic pressure period $T_L$. The low acoustic pressure period $T_L$ is a time duration also starting from the reference time. Thus, in the case of FIG. 10, after the low acoustic pressure transmission has been continued for $T_L$=6 sec. since the reference time, the transmission is switched to the high acoustic pressure transmission.

Herein, seconds are used as a pre-set unit for the selection time $t_s$ and the low acoustic pressure period $T_L$; however, it may be configured in such a manner that these values are set in the unit of the number of frames.

When the respective times and time durations, etc. are set as shown in FIG. 10 by the pre-operation of imaging, the scan sequence is started by manipulating the start switch 13c, according to which the high acoustic pressure ultrasonic transmission is performed for $T_H$=0.5 sec. and the low acoustic pressure ultrasonic transmission is performed for $T_L$=6 sec. repetitively. In this example case, a replenishment image obtained from these scans is displayed, and the selected image is captured about 2 sec. later since the reference time to be displayed on the monitor 14 concurrently in the mode, for example, as the one shown in FIG. 9B. Further, low acoustic pressure irradiation is performed for 6−2=4 sec. continuously from the capturing of the selected image, so that the state of replenishment is shown as a replenishment image. It is thus possible to observe the state of replenishment in real time, in particular, fine perfusion at the level of capillaries in real time, for a longer period (6 sec.) than in the first image generating and displaying method.

The scans and the generation and display of images are continued until the operator manipulates the stop switch 13d shown in FIG. 10.

Figure 9B:
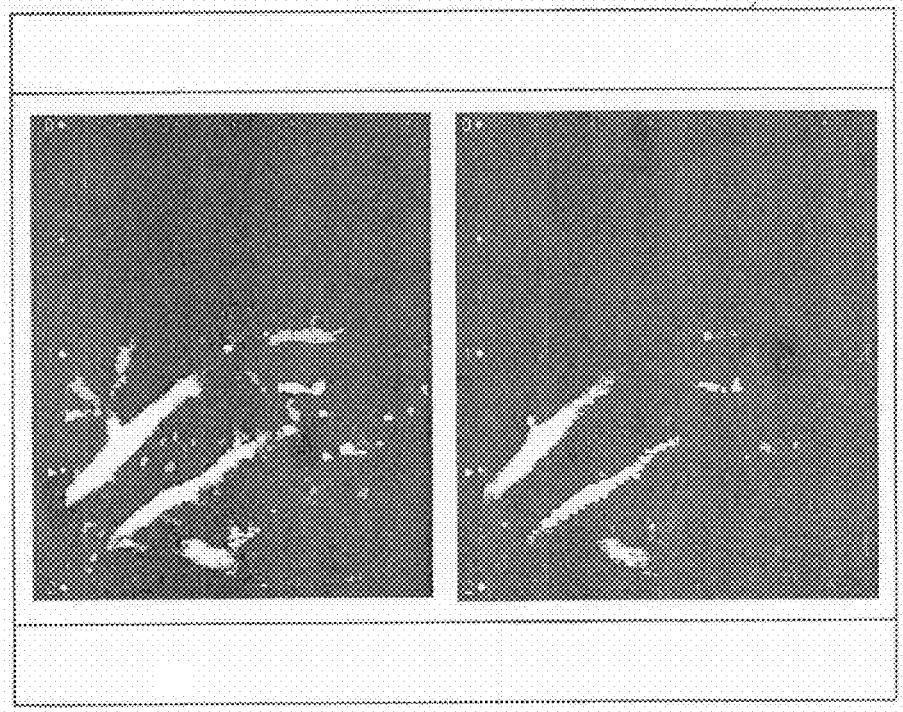
FIG. 9B is a view showing the monitor 14 on which arbitrary replenishment images having different time-phases are displayed concurrently.
Figure 11:
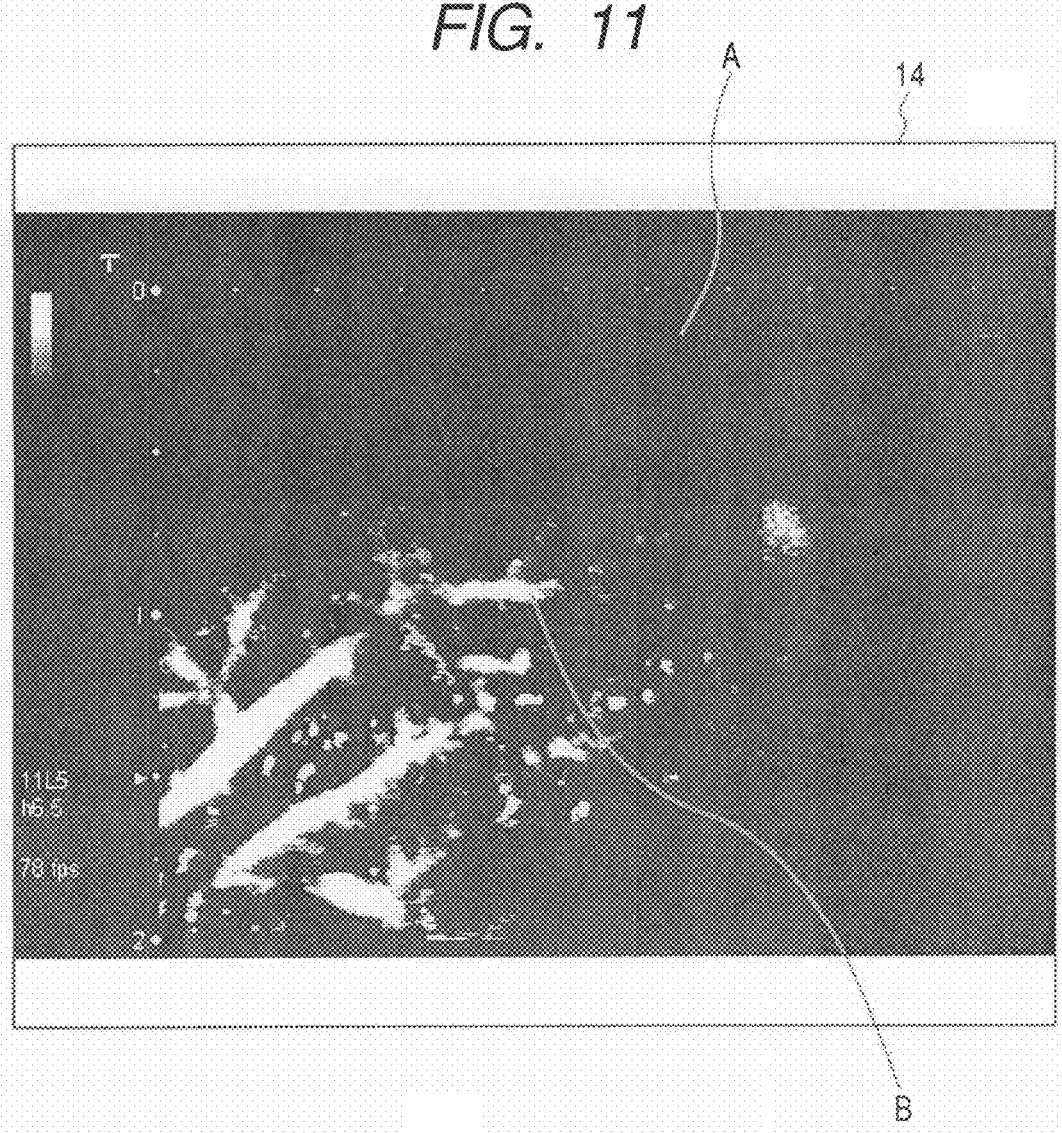
FIG. 11 is a view showing the monitor 14 on which the replenishment image A and the pre-flash image B are superimposed.

The display mode of an image according to the first and second image generating and displaying methods is not limited to those of FIG. 9A and FIG. 9B. For example, as is shown in FIG. 11, it may be a display mode in which the replenish image B and the pre-flash image A or the replenishment image and the selected image are superimposed for display. Such a display mode can enhance the visibility further. In addition, in any display mode, it is possible to make any of the replenishment image, the pre-flash image, and the selected image as a non-display image or back into a display image at arbitrary timing as needed.

(Diagnostic Information Extracting Function)

The diagnostic information extracting function provided to the ultrasonic diagnostic apparatus 10 will now be described.

The diagnostic information extracted by this function includes a blood flow image obtained by the scan sequence (including an image at the level of capillaries), and a histological, physical quantity of a blood flow obtained from the blood flow image. The following description will describe extracting methods for extracting a blood flow image and a histological, physical quantity of a blood flow in this order. Each method is particularly useful in displaying the aforementioned replenishment image or the like.

A suitable blood flow image including an image at the level of capillaries can be extracted with the use of maximum value holding processing, weight update processing, and other luminance holding computations described below. Firstly, the maximum value holding processing performed on n replenishment images for frames $F_1$ through $F_n$ included in the same period $T_L$ will be described. The maximum value holding processing performed on images for the frames $F_1$ through $F_n$ referred to herein is defined as a computation to generate a new image by selecting a maximum value $P_{max}(x, y)$ among spatially corresponding luminance values in the respective frames $F_1$ through $F_n$.

To be more specific, the replenishment image for a given frame $F_i$ (i is an integer satisfying 1≦i≦n) comprises a set of spatially mapped luminance values $P_i(x, y)$, or a set of mere one-dimensional sequence data $P_i(x)$ of luminance values. The values of $P_i(x, y)$ or $P_i(x)$ may be the signal strength, signal amplitude, raw data values of RF data or the like instead of luminance; however, the luminance values are adopted herein. Generally, the respective data values having large numerical values means a higher level of echo signals. By exploiting the respective data values as such, the maximum value of the luminance values for all the pixels in the spatially corresponding frames $F_1$ through $F_n$ is selected, and a computation is performed to generate a new image. This computation can be expressed by Equation (1):

$$P_{max}(x,y)=\max[P_1(x,y), \ldots, P_n(x,Y)] \tag{1}$$

When the maximum value holding processing is used for a replenishment image, processing is performed in accordance with Equation (1) above each time a new frame belonging to the same low acoustic pressure period $T_L$ is acquired, and the resulting image is displayed as a replenishment image. To the operator (observer), the image obtained in this manner seems as if it were showing a way in which capillaries are sequentially contrasted with time.

In this instance, it should be noted that when the maximum value holding processing is performed, only the images within 1 to 2 sec. from the reference time have to be used. Because when images over 2 sec. are included, the microvascular structure is covered and hidden as is shown, for example, in FIG. 3, which limits the advantages of contrast enhancement only as a domain.

The algorithm to achieve the maximum value holding processing is not limited to the one described above. For example, the same advantages can be achieved by the algorithm described below.

That is, given $P_i(x, y)$ as the pixel luminance at each coordinate in the frame $F_i$ for a current tomographic image, and $P_{i-1}(x, y)$ as the pixel luminance in the preceding image frame, then image computation processing expressed by the following equation is performed successively for i=2 to n for these relative two frames.

$$\text{If } P_i(x,y) > P_{i-1}(x,y) \text{ then } P_i(x,y) = P_{i-1}(x,y) \text{ Else } P_i(x,y) = P_{i-1}(x,y)$$

This algorithm is to update the value only for a pixel having a larger luminance value than the counterpart in the image related to the frame in the preceding stage. With the replenishment image or the like obtained in this manner, the operator is also able to observe a way in which capillaries are sequentially contrasted with time.

Another method for a suitable blood flow image including an image at the level of capillaries will now be described. This method is to generate an image by applying weight update processing on n replenishment images for frames $F_1$ through $F_n$ included in the same period $T_L$. The weight update processing referred to herein means a computation expressed by the following equation:

$$\text{If } P_i(x,y) > P_{i-1}(x,y) \text{ then } P_i(x,y) = A^*P_i(x,y) + (1-A)^*P_{i-1}(x,y)$$
$$\text{Else } P_i(x,y) = (A-1)^*P_i(x,y) + A^*P_{i-1}(x,y)$$

By setting A to a value less than one and approximating to one (for example, 0.99), there can be expected functions that the maximum value is held for a short time (in this case, a time interval between the frame in the preceding stage and the current frame), and for a longer time, the luminance held before is attenuated. The operator is thus able to observe a way in which capillaries are sequentially contrasted with time from a replenishment image or the like obtained according to this method.

Incidentally, such maximum value holding processing or the like adopts computation means that projects a maximum value or an updated value in the time direction. Hence, effective time information cannot be obtained by displaying a resulting image intact after it has undergone the aforementioned processing.

In order to eliminate this problem, the present embodiment adopts hue display processing, which is particularly effective in displaying a replenishment image or the like having undergone the aforementioned processing. According to the hue display, images are displayed in different colors for time segments prespecified by the operator, which makes it possible to visually confirm which luminance displayed in the final image belongs to which time segment. The following description will describe the contents of the hue display processing in an example case where two time segments (a first time segment and a second time segment) are specified.

The operator first specifies a time at which the low acoustic pressure period $T_L$ is divided to the first time segment and the second time segment. Herein, 2 sec. from the reference time is set as the dividing time, and a segment before the dividing time is referred to as the first time segment and a segment after the dividing time is referred to as the second time segment.

In the course of forward-feeding the images in the image memory, in a case where the current frame $F_n$ is present in the first time segment, the maximum value holding processing, for example, is applied to the frames $F_1$ through $F_n$ (that is, from the first frame to the current frame present in the first time segment), and an image A is generated as a result.

In a case where the current frame $F_n$ is present within the second time segment, the luminance value holding computation is applied to the frames $F_1, \ldots, F_n$ (that is, from the first frame to the current frame present in the first time segment and the second time segment) to generate an image A', while the image A is being generated.

Figure 12:
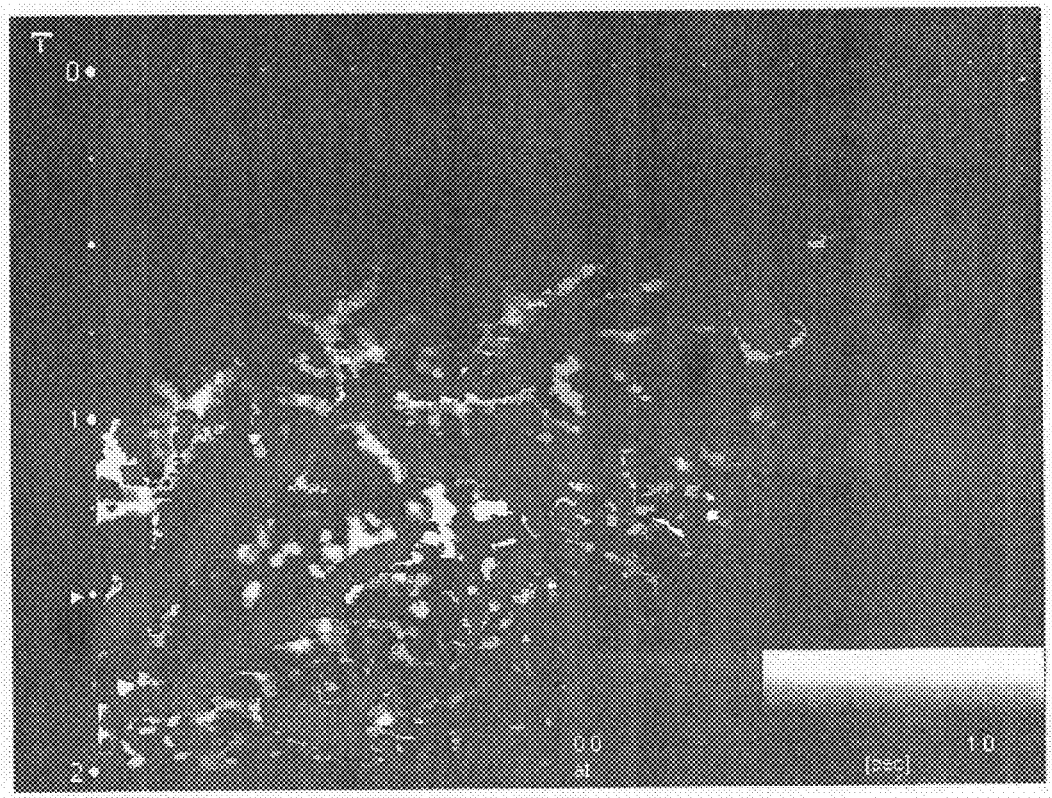
FIG. 12 shows a superimposed image in two hues generated through hue display processing.

Differential computation processing, that is, (image A'−image A), is then performed to generate a resulting image B. Finally, hue conversion is performed in such a manner that, for example, the image A is converted to a hue A (for example, red), and the resulting image B is converted to a hue B (for example, yellow). A superimposed image of these images is generated, and as is shown in FIG. 12, displayed on the monitor 14 as a replenishment image or the like.

The operator, by observing the replenishment image shown in FIG. 12, becomes able to readily and rapidly understand that the hue A is the region into which the contrast medium has flown within 2 sec. from the reference time (first time segment), and the hue B is the region into which the contrast medium has flown 2 sec. later since the reference time (second time segment).

According to the hue display processing, even when the luminance value holding computation, such as the maximum value holding processing and the weight update processing, is performed, it is possible to provide a suitable blood flow image containing information at the level of capillaries in the mode easy for the operator to observe, without losing time information.

While the hue display processing using two time segments has been described by way of example, it goes without saying that this method is applicable to an arbitrary number of time segments. The procedure in such a case is that the processing described above is performed for adjacent two segments, and N images each having a different hue are obtained, after which a superimposed image of these N images is generated and displayed as a final image. For example, in the case of a superimposed image where N=4 (for example, four colors including red, yellow, green, and blue), an image as shown in FIG. 13 is displayed on the monitor 14.

Figure 13:
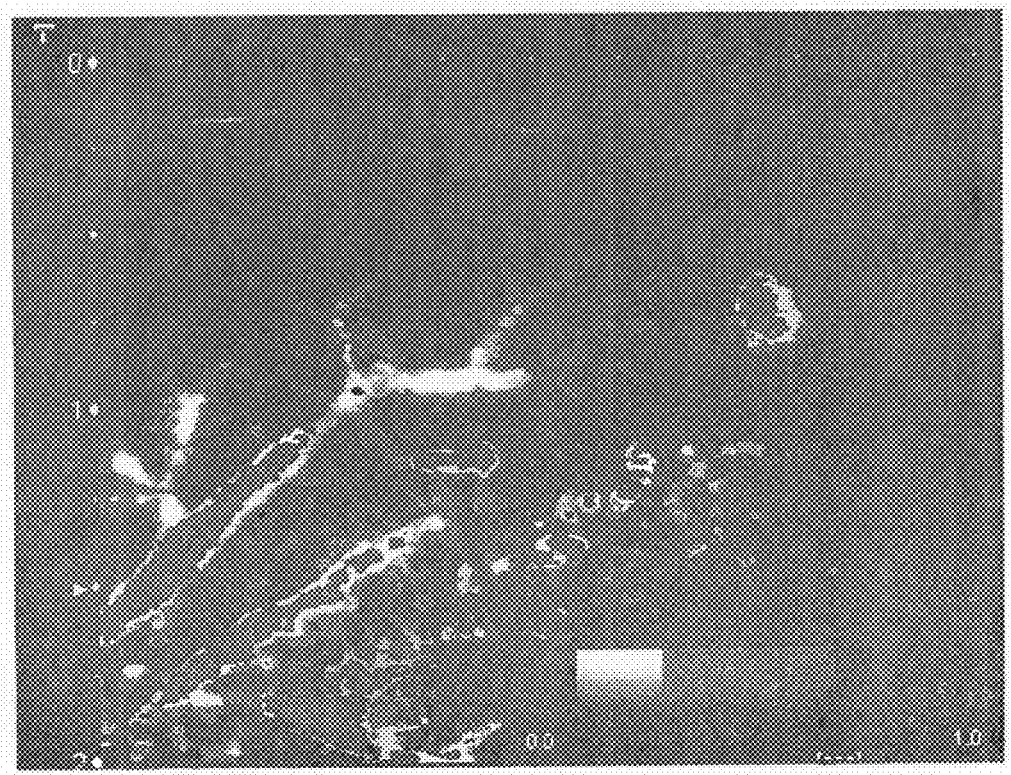
FIG. 13 shows a superimposed image in four hues generated through the hue display processing.

When an image having undergone the hue display processing is displayed, it is preferable to display concurrently a color scale bar indicating the relation between the hues and the time segment or the elapsed time as are shown in FIG. 12 and FIG. 13.

(Calculation of Histological, Physical Quantity)

Calculation processing for a histological, physical quantity of a blood flow based on the blood flow image obtained by the scan sequence will now be described.

Figure 3:
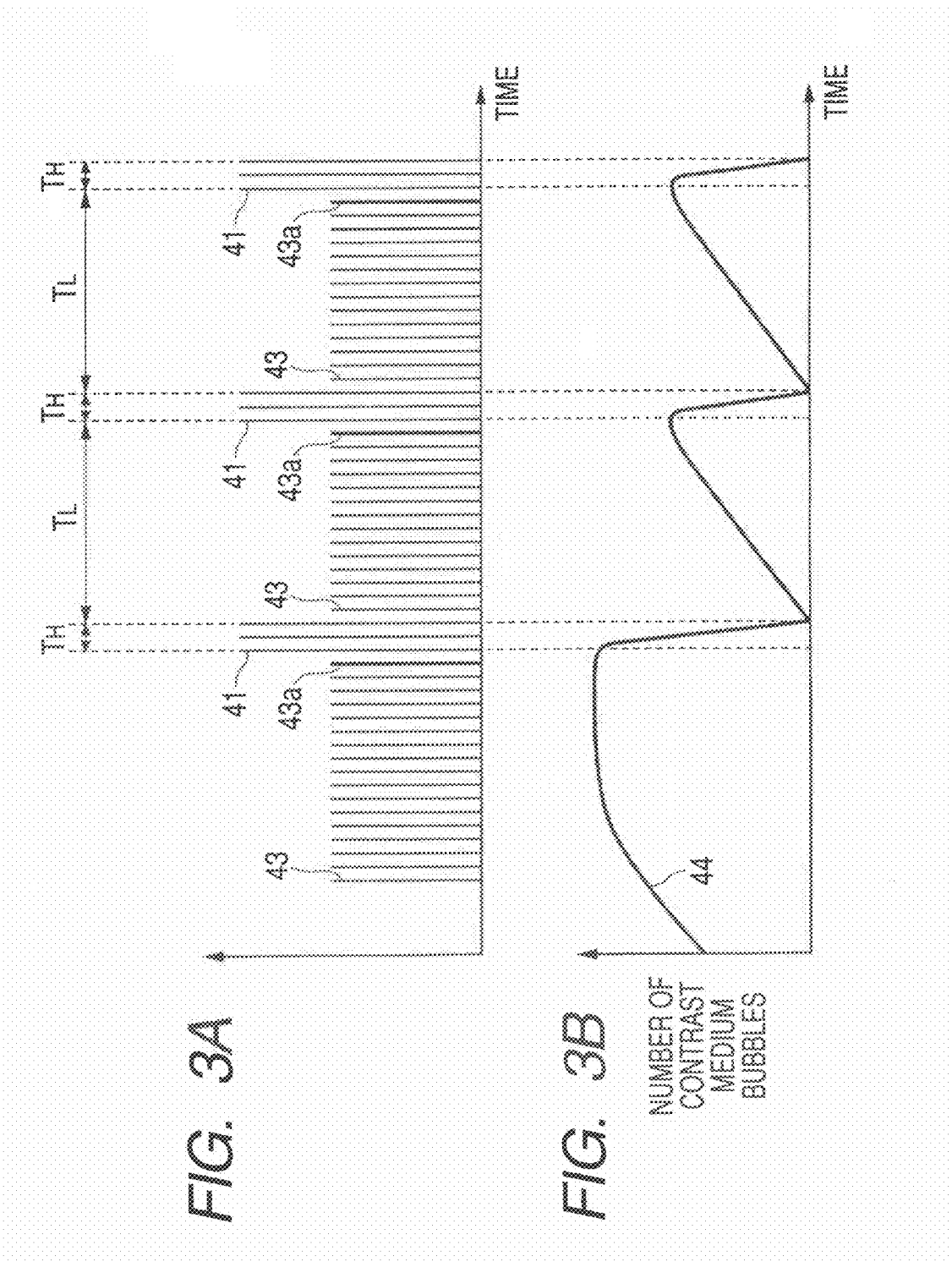
FIG. 3A and FIG. 3B are views used to explain a basic scan sequence the ultrasonic diagnostic apparatus 10 performs and the number of contrast medium bubbles at scans according to the sequence.

The principle of the physical quantity calculation processing is as follows. That is, in a case where the low acoustic pressure ultrasonic transmission has been performed for a sufficient time, $T_m$ sec., the pre-flash image 43 shown in FIG. 3 is an image of a tomographic plane filled with blood flows, and the signal luminance within this image is therefore thought to be the maximum value at the region in question. Also, it goes without saying that $T_m$ sec. is needed for each pixel luminance within the replenishment image immediately after high acoustic pressure irradiation to restore to, or nearly to that in the pre-flash image.

Assume that, during a given time duration, the luminance value of each pixel in the replenishment image reaches C % (for example, 50%) of that in the pre-flash image, then a shorter time than $T_m$ is naturally given to this time duration. The time duration during which the luminance value of each pixel in the replenishment image reaches C % of the luminance value of the counterpart pixel in the pre-flash image is defined as a quasi-recovery time $T_C$. JP-A-11-89839, for example, has reported the technique to display hues with a consideration given to such a time duration for the pixel to reach C % luminance value. The histological meaning of the recovery time per se, however, is ambiguous by merely setting the numerical value to C % arbitrarily, which may not contribute much to clinical scenes.

For this reason, in this embodiment, the region having reached the quasi-recovery time $T_C$ is displayed in hue, and an average passing time $T_{mtt}$ (an average time needed for a blood flow to pass through the tomographic plane), that is, a histological, physical quantity of a blood flow, is predicted from the quasi-recovery time $T_C$ to be presented to the operator.

Figures 14, 15:
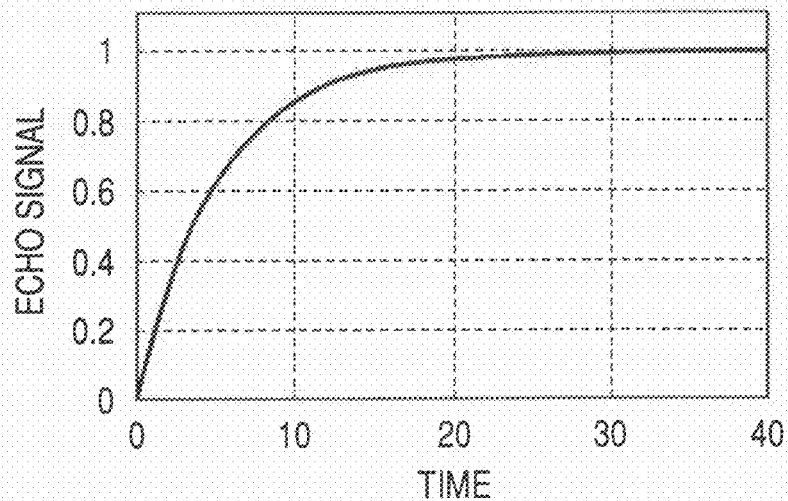
FIG. 14 is a graph indicating a change of a contrast medium signal after replenishment, expressed by Equation (2)
FIG. 15 is a table showing the relation between n and $V_c/V_0$ calculated in accordance with Equation (7)

The inventor discovered from his studies that when a change of echo signals with time in an organ region within the replenishment image is observed, it shapes a curve as shown in FIG. 14. This curve can be satisfactorily approximated by Equation (2):

$$V(t)=V_0(1-e^{-\beta t}) \quad (2)$$

where V(t) is a linear signal strength before logarithmic conversion, $V_0$ is a signal strength after a sufficient time elapsed (for example, a signal strength of the pre-flash image), β is a constant, and t is a time duration. In particular, β is related to a flow rate (the reciprocal number 1/β is related to the passing time), and β becomes larger where the flow rate is high, and smaller where the flow rate is low.

When an increase in luminance of the replenishment image is represented by the curve expressed by Equation (2) above, the average passing time $T_{mtt}$ is equal to 1/β. Assume that the signal strength reaches $V_C$ $t_C$ sec. later, then, Equation (3) below is established from Equation (2) above:

$$V_C=V_0(1-e^{-\beta t_C}) \quad (3)$$

By solving Equation (3) above for β, we get Equation (4):

$$\beta=-1/t_C(\ln(1-V_C/V_0)) \quad (4)$$

Thus, the average passing time $T_{mtt}$ is given by Equation (5):

$$T_{mtt}=1/\beta=-t_C(1/\ln(1-V_C/V_0)) \quad (5)$$

Equation (5) apparently looks complicated; however, $T_{mtt}=t_C$ is established if $V_C$ takes the value of Equation (6):

$$V_C=V_0((e-1)/e)=0.63212*V_0 \quad (6)$$

In other words, an elapsed time (quasi-recovery time $T_C$ needed to reach C=63%) from the reference time, at which the replenishment image becomes about 0.63 time of pre-flash image, means the average passing time of the blood flow related to the patient.

This result can be extended further. That is, let $t_C$ be a time at which $V_C$ satisfies Equation (7):

$$V_C=V_0((e^{1/n}-1)/e^{1/n}) \quad (7)$$

In this instance, there is established a relational expression, $T_{mtt}=t_C*n$, between the average passing time $T_{mtt}$ and $t_C$. In other words, by finding the quasi-recovery time $t_C$, which is shorter than the original average passing time $T_{mtt}$, and multiplying $t_C$ by n, it is possible to obtain the average passing time $T_{mtt}$ without waiting for the physical time to elapse. According to this extension, Equation (6) above can be deemed as Equation (7), where n=1.

FIG. 15 is a correspondence table indicating the relation between n and the value of $V_C/V_0$ computed in accordance with Equation (7) above. In practice, a diagnostic image is often displayed in the unit of decibels, and the drawing shows values converted to decibels for $V_C/V_0$ as well. This correspondence table is stored in the internal storage device 29.

In this embodiment, a desired number for n is selected first and $t_C$ needed for each pixel on the replenishment image to reach the value of $V_C/V_0$ corresponding to n is then computed, according to the logic described above. A value obtained by multiplying the resulting $t_C$ by n is presented to the operator as the average passing time $T_{mtt}$, so that the average passing time $T_{mtt}$ can be predicted without having to wait for contrast enhancement up to the pre-flash image.

To be more specific, at least one value for $V_C/V_0$ to be referred to is set first. Herein, assume that $V_C/V_0=0.39$ (n=2) is set.

Subsequently, the signal strength of each pixel in the pre-flash image obtained through imaging is stored as $P_0=(x, y)$, while the pre-flash image is displayed on the monitor 14.

Also, it is judged whether $P_i(x, y)/P_0(x, y) > 0.39$ is established for the signal strength $P_i(x, y)$ of each pixel in the replenishment image for each frame while the replenishment image is being displayed like a moving picture. When it is judged that $P_i(x, y)/P_0(x, y) > 0.39$ is established, hue display is performed by coloring the pixel with a new color tone (red). Also, while the replenishment image is being displayed, the numerical value of $T_C \div n$ (sec.), the product of the elapse time $T_C$ from the reference time and n (n=2, herein), is displayed as the average passing time $T_{mtt}$. When the high acoustic pressure transmission and the low acoustic pressure transmission are performed repetitively, the same processing is performed repetitively.

According to the method as described above, the operator, by visually confirming that specific pixels on the screen are displayed concurrently at the timing at which these pixels are colored, becomes able to visually confirm with ease that the average passing time $T_{mtt}$ for the region of the subject corresponding to these pixels is equal to $T_C*n$ (sec.) or less. The operator thus does not have to wait for the average passing time $T_{mtt}$ to elapse, and is able to predict the average passing time $T_{mtt}$, that is, a histological, physical quantity of a blood flow, in one n'th time of the actual time duration, rapidly at high accuracy with ease.

(Series of Imaging Operations)

Figure 16:
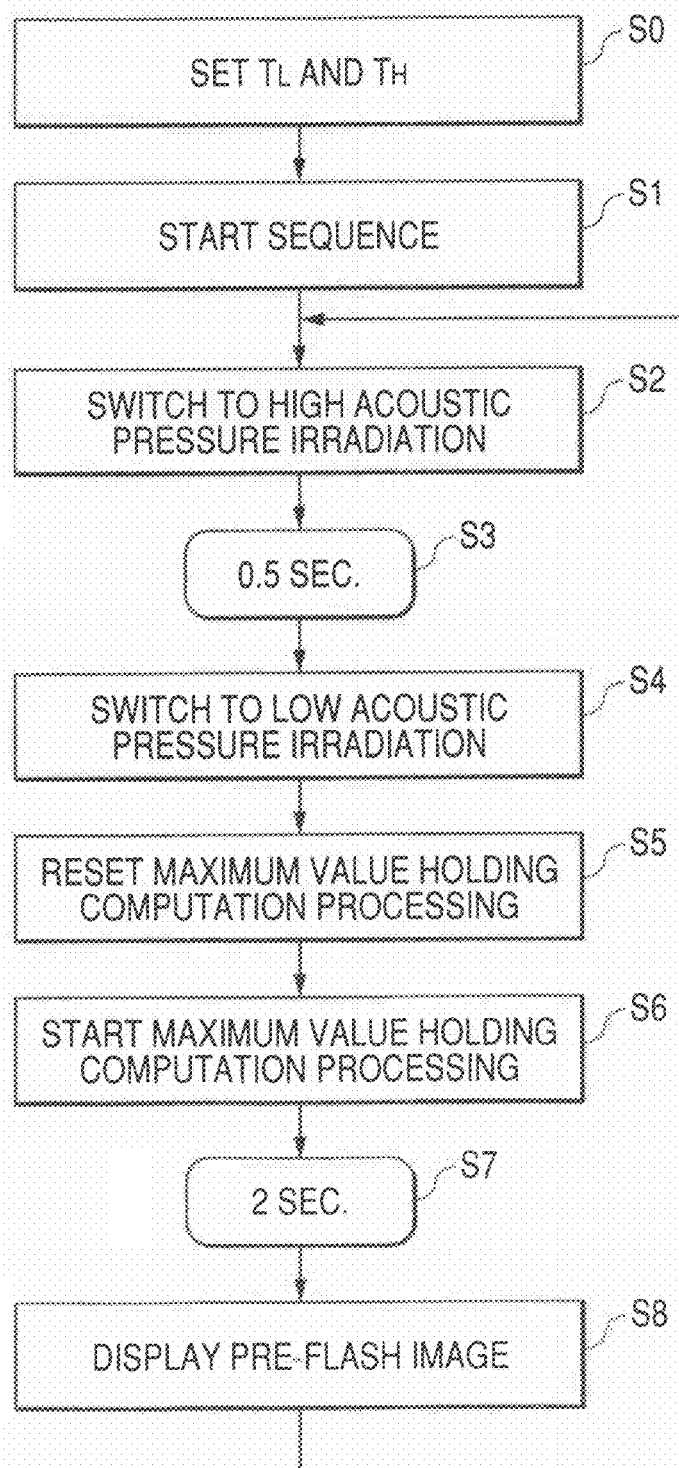
FIG. 16 is a flowchart detailing the flow of processing for imaging operations when a first image generating and displaying method is used.
Figure 17:
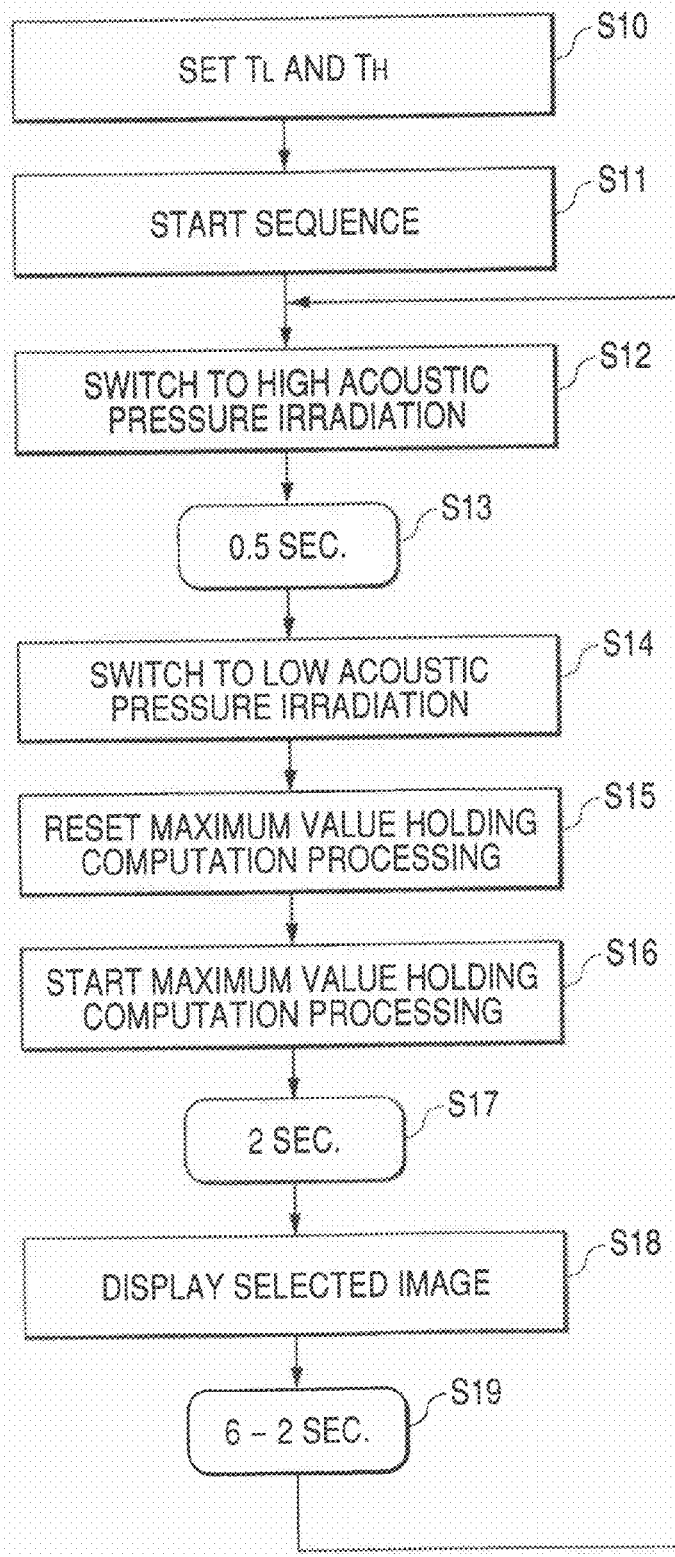
FIG. 17 is a flowchart detailing the flow of processing for imaging operations when a second image generating and displaying method is used.

A series of imaging operations to perform the respective functions described above will now be described with reference to FIG. 16 and FIG. 17.

Firstly, imaging operations when the first image generating and displaying method is used will be described. FIG. 16 is a flowchart detailing the flow of the imaging processing when a blood flow image is extracted using the first image generating and displaying method. Initially, a high acoustic pressure transmission time is set to 0.5 sec. and a low acoustic pressure transmission time is set to 2 sec. (Step S0). After the settings, at an instruction from the operator via the start switch 13c of FIG. 8, the scan sequence is started, according to which the high acoustic pressure transmission is performed for 0.5 sec. and the low acoustic pressure transmission is performed for 2 sec. repetitively (Step S1). The scan conditions or the like are then switched to those of the initial high acoustic pressure transmission (Step S2), and the high acoustic pressure transmission is performed for 0.5 sec. (Step S3).

When the high acoustic pressure transmission has been performed for 0.5 sec., the scan conditions are switched to those of the low acoustic pressure transmission (Step S4), while at the same time, in a case where the luminance value holding computation has been applied on the replenishment image in the preceding stage, information related to the luminance vale holding computation in the preceding stage is reset (Step S5). After the information is reset, the low acoustic pressure ultrasonic transmission as well as new luminance value holding computation is started (Step S6), and continued for 2 sec. (Step S7). In the course from Steps S5 through S7, a replenishment image, which is obtained through the low acoustic pressure ultrasonic transmission and on which the luminance value holding computation is applied, is displayed on the monitor 14 in real time like a moving picture.

The pre-flash image is captured 2 sec. later since the start of the low acoustic pressure transmission, and displayed on the monitor 14 like a still image together with the replenishment image (Step S8). When the same scan sequence is repeated thereafter, processing from Steps S2 through S8 is performed again. On the other hand, when an end instruction is inputted via the stop switch 13d, the imaging according to the scan sequence is completed.

According to the imaging processing as described above, the pre-flash image, on which a micro-vascular branch structure is extracted due to the luminance value holding computation, is displayed on the monitor 14 each time the low acoustic pressure transmission and the high acoustic pressure transmission are repeated. The replenishment image is also displayed on the monitor 14 like a moving picture each time the low acoustic pressure transmission and the high acoustic pressure transmission are repeated. The operator is thus able to observe not only the dynamic state of living organs in real time from the replenishment image, but also the micro-vascular branch structure statically from the pre-flash image. It is thus possible to obtain diagnostic information at the level of micro-vascular branch rapidly in an effective manner.

For the imaging described above, calculation of a histological, physical quantity may be performed instead or together with the luminance value holding computation. In this case, calculation of a histological, physical quantity is performed instead of or in parallel with the luminance value holding computation in Steps S6 and S7, and the result is displayed in real time together with the replenishment image.

Imaging operations when the second image generating and displaying method is used will now be described. FIG. 17 is a flowchart detailing the flow of processing for the imaging operations when the second image generating and displaying method is used. The operator first sets, respectively via the switches 13f, 13a, 13g of FIG. 10, 2 sec. from the reference time as the timing at which a selected image is obtained, 0.5 sec. as a high acoustic pressure transmission time, and 6 sec. as a low acoustic pressure transmission time (Step S10). After the settings, at an instruction via the start switch 13c, the scan sequence is started, according to which the high acoustic pressure transmission is performed for 0.5 sec. and the low acoustic pressure transmission is performed for 6 sec. repetitively (Step S11). The scan conditions or the like are then switched to those of the initial high acoustic pressure transmission (Step S12), and the high acoustic pressure transmission is performed for 0.5 sec. (Step S13).

When the high acoustic pressure transmission has been performed for 0.5 sec., the scan conditions are switched to those of the low acoustic pressure transmission (Step S14), while at the same time information related to the luminance vale holding computation in the preceding stage is reset (Step S15). After the information is reset, the low acoustic pressure ultrasonic transmission as well as new luminance value holding computation is started (Step S16), and continued for 2 sec. (Step S17). In the course from Steps S15 through S17, a replenishment image is displayed on the monitor 14 in real time like a moving picture.

The selected image is captured 2 sec. later since the start of the low acoustic pressure transmission, and displayed on the monitor 14 like a still image together with the replenishment image (Step S18). The low acoustic pressure ultrasonic transmission is continued for further 4 sec. (6–2 sec.), and a corresponding replenishment image is displayed on the monitor 14 in real time like a moving picture (Step S19).

When the same scan sequence is repeated thereafter, processing from Steps S12 through S19 is performed again. On the other hand, when an end instruction is inputted via the stop switch 13d, the imaging according to the scan sequence is completed.

According to the imaging processing described above, the same advantages as those achieved by the imaging when the first image generating and displaying method is used can be achieved. For the imaging described above, calculation of a histological, physical quantity may be also performed instead of or together with the luminance value holding computation.

In this case, calculation of a histological, physical quantity is performed instead of or in parallel with the luminance value holding computation in Steps S16 through S19, and the result is display in real time together with the replenishment image.

Second Embodiment

A second embodiment of the invention will now be described. This embodiment is to perform the first or second image generating and displaying method in the middle of or after the imaging.

As has been described, the ultrasonic diagnostic image obtained and observed in real time with the apparatus is also stored in the image memory 26. Hence, when the operator has observed images for a certain time, he generally stops the ultrasound scans through an input from a freeze button on the control panel, so that a series of tomographic images in the image memory 26 are played back. These images can be displayed either like a still image or a moving picture. Also, as is shown in FIG. 18, the operator is able to control the playback, stop, fast forwarding, backward feeding, etc. at arbitrary timing by means of playback buttons 13r and the track ball 13s provided to the input device 13.

In addition, as is shown in FIG. 18, in the case of the apparatus 10 of this embodiment, the input device 13 is provided with a maximum value holding button 13j used for the aforementioned luminance value holding computation, for example, for use in specifying whether the maximum value holding processing is to be enabled. While the maximum value holding button 13j remains OFF, conventional ultrasonic diagnostic images are displayed on the monitor frame by frame. On the other hand, when the maximum value holding button 13j is switched ON, a tomographic image frame being displayed at that point in time is registered as the reference image ($F_1$). Subsequently, as the operator feeds the display image forward to $F_2$, $F_3$, and so forth, the image generating circuit 25 applies the aforementioned maximum value holding computation on the images, including the reference image $F_1$ to the currently displayed tomographic image frame $F_n$ (n>1), and displays the result on the monitor 14.

The first image generating and displaying method or the like in the middle of or after the imaging as described above is also applicable to the time-sequential backward playback (that is, backward feeding of frames). For example, when the operator have $F_m$ (m<n) be displayed through backward feeding of played back images after a tomographic image frame $F_n$(n>1) is displayed, the image generating circuit 25 only has to perform the maximum value holding processing from $F_n$ to $F_m$ to generate an image again.

It should be noted that the obtained image may be susceptible to motions, such as breathing and heat beats, which gives rise to an offset of corresponding positions between the frames. When the maximum value holding computation or the like is performed directly in such a case, an adequate result may not be obtained.

In order to eliminate this problem, the ultrasonic diagnostic apparatus 10 is furnished with an image blurring adjusting function to adjust the position correspondence between frames, so that the luminance value holding processing, such as the maximum value holding processing, can be performed adequately. This adjustment is performed by depressing a fine-adjustment button 13k shown in FIG. 18. More concrete operations are as follows.

For example, in a case where the maximum value holding computation is currently applied to frames $F_1$ through $F_n$, then the mode is switched to the fine-adjustment mode when the fine-adjustment button 13k is depressed. In this fine-adjustment mode, for superimposed positions between a maximum value holding image (image A) of $F_1$ through $F_{n-1}$ and an image of $F_n$ (image B), a fine-adjustment displacement (dx, dy), which is a quantity of offset between the image A and the image B that needs to be cancelled out, is generated through manipulation of the track ball 13s or the like. Then, the position is fine-adjusted by mapping (x+dx, y+dy) of the image B to the coordinate (x, y) of the image A, and the fine-adjustment is confirmed by depressing the fine-adjustment button 13k again.

According to the configuration as above, the operator is able to perform the first or second image generating and displaying method at any desired timing. Also, in the event of an offset in position between frames, fine-adjustment is performed at arbitrary timing, so that more reliable diagnostic information can be obtained.

Additional advantages and modifications will readily occur to those skilled in the art. Therefore, the present invention in its broader aspects is not limited to the specific details, representative devices, and illustrated examples shown and described herein. Accordingly, various modifications may be made without departing from the sprit or scope of the general inventive concept as defined by the appended claims and their equivalents.

What is claimed is:

1. An ultrasonic diagnostic apparatus comprising:
   an ultrasonic probe which transmits ultrasonic waves to a subject injected with contrast medium bubbles, receives reflected ultrasonic waves from the subject, and generates echo signals on the basis of the received ultrasonic waves;
   a transmission unit configured to perform, via the ultrasonic probe, a series of first transmissions for a plurality of frames at a first acoustic pressure, which is an acoustic pressure not to destroy substantially the contrast medium bubbles but to obtain an image of a blood flow circulation, and to perform a series of second transmissions for a plurality of frames at a second acoustic pressure to destroy the contrast medium bubbles;
   a control unit configured to control the transmission unit in such a manner that the series of first transmissions and the series of the second transmissions are performed alternatively; and
   an image generating unit configured to generate a first image by performing a luminance value holding computation using echo signals of at least two frames obtained in the first transmissions.

2. The ultrasonic diagnostic apparatus according to claim 1, wherein the image generating unit generates the first image after initializing the luminance value holding computation synchronized with the first transmissions.

3. The ultrasonic diagnostic apparatus according to claim 1, wherein:
   the image generating unit generates the first image according to an echo signal obtained through the first ultrasonic transmission corresponding to a frame, immediately before the plural first ultrasonic transmissions are switched to the second ultrasonic transmission.

4. The ultrasonic diagnostic apparatus according to claim 1, wherein:
   the image generating unit generates the first image according to an echo signal obtained through the first ultrasonic transmission at a second point in time at which a predetermined time period has elapsed since a first point in time at which the second ultrasonic transmission is switched to the plural first ultrasonic transmissions.

5. The ultrasonic diagnostic apparatus according to claim 4, further comprising:
   a setting unit to set the second point in time to an arbitrary time,
   wherein the image generating unit generates the first image according to an echo signal obtained through the first ultrasonic transmission at the second point in time set by the setting unit.

6. The ultrasonic diagnostic apparatus according to claim 1, wherein:
   the image generating unit updates the first image time-sequentially by performing the luminance value holding computation from time to time, using echo signals for respective frames obtained through the plural first ultrasonic transmissions.

7. The ultrasonic diagnostic apparatus according to claim 1, wherein:
   the image generating unit generates a second image using an echo signal corresponding to an arbitrary frame among echo signals of plural frames obtained through the plural first ultrasonic transmissions; and
   a display unit displays the first image and the second image concurrently.

8. The ultrasonic diagnostic apparatus according to claim 1, wherein:
   a display unit displays the first image as a moving picture and the second image as a still image.

9. The ultrasonic diagnostic apparatus according to claim 1, wherein:
   a display unit superimposes the first image and the second image for display.

10. The ultrasonic diagnostic apparatus according to claim 1, wherein the image generating unit generates the first image by:
    generating a first intermediate image by performing a luminance value holding computation according to echo signals of m frames obtained through the plural first ultrasonic transmissions, and generating a second intermediate image by performing the luminance value holding computation according to echo signals of n (m<n) frames obtained through the plural first ultrasonic transmissions;
    generating a differential image between the second intermediate image and the first intermediate image;
    converting the first intermediate image into a first hue and the differential image to a second hue; and
    synthesizing the first intermediate image converted to the first hue and the differential image converted to the second hue.

11. The ultrasonic diagnostic apparatus according to claim 1, wherein:
    the luminance value holding computation is a maximum value holding computation, by which the first image is generated by holding a maximum value among values of the echo signals at spatially corresponding positions between the plural frames.

12. The ultrasonic diagnostic apparatus according to claim 1, wherein:
    the luminance value holding computation is a weight update computation, by which the first image is generated by adding a weight to each of the echo signals at spatially corresponding positions between adjacent two frames among the plural frames.

13. The ultrasonic diagnostic apparatus according to claim 1, wherein:
    in a case that the second ultrasonic transmission is performed, the image generating unit generates the first image by initializing the luminance value holding computation and according to echo signals obtained through the plural first ultrasonic transmissions after the second ultrasonic transmission.

14. The ultrasonic diagnostic apparatus according to claim 1, further comprising:
a selection unit to select a reference frame at which the luminance value holding computation is started,
wherein the image generating unit starts the luminance value holding computation from the selected reference frame.

* * * * *